(12) United States Patent
Cigaina et al.

(10) Patent No.: US 6,411,842 B1
(45) Date of Patent: Jun. 25, 2002

(54) IMPLANT DEVICE FOR INTERNAL-EXTERNAL ELECTROMYOGRAPHIC RECORDING, PARTICULARLY FOR THE IN VIVO STUDY OF ELECTROMOTOR ACTIVITY OF THE DIGESTIVE SYSTEM

(76) Inventors: Valerio Cigaina, Via IV Novembre 3/a, 1-3150 Villobra (Treviso); Francesco Ferraro, Via Magnano 21, 1-10100 Piverone (Torino), both of (IT)

( * ) Notice: Subject to any disclaimer, the term of this patent is extended or adjusted under 35 U.S.C. 154(b) by 0 days.

(21) Appl. No.: 09/449,165

(22) Filed: Nov. 24, 1999

(30) Foreign Application Priority Data

Nov. 26, 1998 (IT) .......................................... MI98A2561

(51) Int. Cl.⁷ ............................................ A61B 5/0488
(52) U.S. Cl. ...................................... 600/546; 600/377
(58) Field of Search ........................ 607/48, 49, 50–52, 607/62, 133; 600/373, 377, 546

(56) References Cited

U.S. PATENT DOCUMENTS 5,233,999 A * 8/1993 Dellacorna et al. .......... 600/546
5,373,852 A * 12/1994 Harrison et al. ............ 600/546

* cited by examiner

*Primary Examiner*—George R. Evanisko
(74) *Attorney, Agent, or Firm*—Herbert Dubno

(57) ABSTRACT

Implant device for internal-external electromyographic recording of the electromotor activity of the digestive system, being of the type that comprises at least one sensor implanted in the viscera to record its electric activity and to provide a device for analysis in vivo of the electric activity of the tract, capable of giving the patient normal freedom of movement.

11 Claims, 3 Drawing Sheets

IMPLANT DEVICE FOR INTERNAL-EXTERNAL ELECTROMYOGRAPHIC RECORDING, PARTICULARLY FOR THE IN VIVO STUDY OF ELECTROMOTOR ACTIVITY OF THE DIGESTIVE SYSTEM

FIELD OF THE INVENTION

The invention relates to a new implant device for internal-external electromyographic recording, particularly for in vivo study of the electromotor activity of the digestive system.

BACKGROUND OF THE INVENTION

Almost 70% of the diseases of the gastroenteric system are classified as functional, which is to say that the cause of the patient's problem is secondary to a malfunction of the gastroenteric canal, whether in digestive or motor terms.

The histological characteristic of a muscular component present along the entire length of the digestive system, which is responsible for its motor activity, has as its counterpart an associated electric activity that is secondary to the depolarization of the musculature itself.

They are the mirror image of one another, under both normal and pathological conditions.

The gastroenterologist's need to study the digestive system in terms of both the electric and the motor profile (the associated electric activity) has now become imperative, since, depending on the functional or associated disturbances, there is a specific disturbance of the electromotor activity.

Electromyography is the recording of intra-cellular or extra-cellular potentials generated by cyclical electrical changes across the membranes of smooth muscle cells.

OBJECTS OF THE INVENTION

An object of the invention is to provide an apparatus which enables the study of extra-cellular potential, which is to say what can be picked up by an electrode inserted in the extra-cellular fluid circulating in the mass of smooth muscle cells and which acts as a syncytium.

Essential to that goal is insertion of the electrodes, whose number and modalities of use distinguish the recording as mono- or bipolar.

The need to study the electromotor activity of the digestive system in vivo and under conditions of freedom for the patient under study is limited by what the current technology has to offer.

The best and most reliable electromyograms of the gastrointestinal tract are obtained by serum electrodes implanted after laparotomy or laparoscopy and directly connected by means of wires to a unit for processing and visualizing the electrical signals.

Surgical implanting of electrodes is, however, not attractive to patients with suspected motor disorders, and, aside from the ethical and practical implications of recording electrical signals in a patient recently operated on and limited in his or her freedom by being anchored to wires connected to a machine, it may result in erroneous conclusions as regards normal motility.

While cutaneous electrodes of the standard gastric transducer available on the market are certainly not invasive and are practice to use, they unfortunately are still limited by the fact that they tie the patient to a machine and pen recording of only one part of the electrical activity, namely the slow wave component.

Lastly, the need to use filters to eliminate disturbances from cardiac electrical activity, from the respiratory diaphragm muscle, and from other viscera may make interpretation of the recorded image fairly operator-dependent.

Hence, the main object of the invention is to provide a new device for internal-external electromyography recording which, unlike those currently known, allows the patient to move with complete freedom during the recording and to conduct his or her life normally.

The invention also has as its object to provide a device of the abovementioned kind with a special feature of being able to be partially or fully implanted so as to reduce to a necessary minimum, if not to eliminate entirely, the fixed internal-external connected between the transducer and the units that process the set of relevant signals.

SUMMARY OF THE INVENTION

These objects are achieved in an implant device for internal-external electromyographic recording of the electromotor activity of the digestive system, which comprises at least one sensor implanted in the viscera to record its electrical activity and having means for analysis in vivo of the electric activity of the system, capable of allowing the patient normal freedom of movement.

These means can consist of at least one conversion unit to convert into radio signals the signals received from at least one sensor and to transmit such radio signals to a unit where they are processed.

At least one such sensor is an electrocatheter and the conversion unit can consist of a self-powered mobile amplifier-transmitter module connected to the electrocatheter by wires and capable of being affixed to the patient's skin.

The module can comprise an amplifier to amplify the signals sent by the electrocatheter; a processor-converter to convert to digital signals the analog signals supplied by the amplifier;

a transmitter—modulator unit to convert the digital signals into radio signals and to transmit them to a fixed receiver; and an antenna that receives the radio signal transmission sent by the transmitter-modulator.

The amplifier can have an input impedance greater than or equal to 100 MOhms, as well as a gain greater than or equal to 200, and is in any case compatible with the type of microprocessor used.

The processor-converter can have a parity greater than or equal to 4 bits, an internal analog-digital converter, input-output ports as a function of the number of channels to be processed, and a full duplex UART port with internal RAM greater than 128 bytes and an external EPROM address.

The clock frequency of the processor can be greater than or equal to 2 MHz.

The fixed receiver can consist of a receiver unit for the signals captured by the antenna on the module, a comparator, a serial interface driver, and an antenna for transmission of radio signals to a unit to process and graphically visualize the signals.

The electrocatheter can be provided with one or more poles to record the electrical activity of the viscera, which is anchored by means of a removable needle.

At least one such radio signal conversion and transmission unit is combined with at least one such sensor in a device that is fully implanted in the viscera and has no connecting wires.

At least one such sensor can consist of an electrode and the radio signal conversion and transmission unit can consist of a unit that, in addition to the sensor, has an amplifier for the signals supplied by the sensor and a processor-converter directly linked to the sensor and capable of converting the analog signals from the latter into radio signals.

The device can be provided with a casing to house the unit and from which casing at least one sensor projects the minimum amount needed to ensure electrical contact with the muscle structure of the viscera. The casing on the implant device can be provided with a clip-off tip, with an end for grasping the device itself, and with wings to hold the device in the wall of the viscera.

The length and maximum lateral dimension of the casing is compatible with the operating canals of gastroscopes, the casing being made of an electrically insulating and biologically compatible material.

The device can include a self-powered mobile unit capable of being affixed to the patient's skin, to receive radio signals sent by the unit and to transmit such signals to a fixed receiver. This mobile unit can comprise:

an antenna that receives the radio signal from the unit;

a receiver unit;

a transmitter section of the transponder which powers the unit;

a transmitter of radio signals to the fixed receiver;

a microprocessor to control and process the mobile unit; and batteries to supply the unit.

The fixed receiver can have a unit to receive the signals sent by the mobile unit, a clipping circuit, a serial interface driver, and an antenna to transmit radio signals to a unit for processing and graphically visualizing the signals.

As regards the current technology in use, the state of the art according to the invention offers the important advantage of freeing the patient subject to internal-external electromyographic examination from being anchored by wires to the fixed part of the device.

The invention also presents the advantage of reducing, and even eliminating, the fixed connections between the internal sensors and the external signal-processing unit.

According to a preferred mode of embodiment, the invention offers the advantage of obviating the conventional need to surgically implant the means for sensing and recording gastrointestinal activity.

It should also be noted at this point that the invention, while used preferably to study the electromotor activity of the gastric viscera, is also advantageously applied to other visceral ducts of the digestive system.

Therefore, the following description of the electromyography device of the invention is not limited to the stomach.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
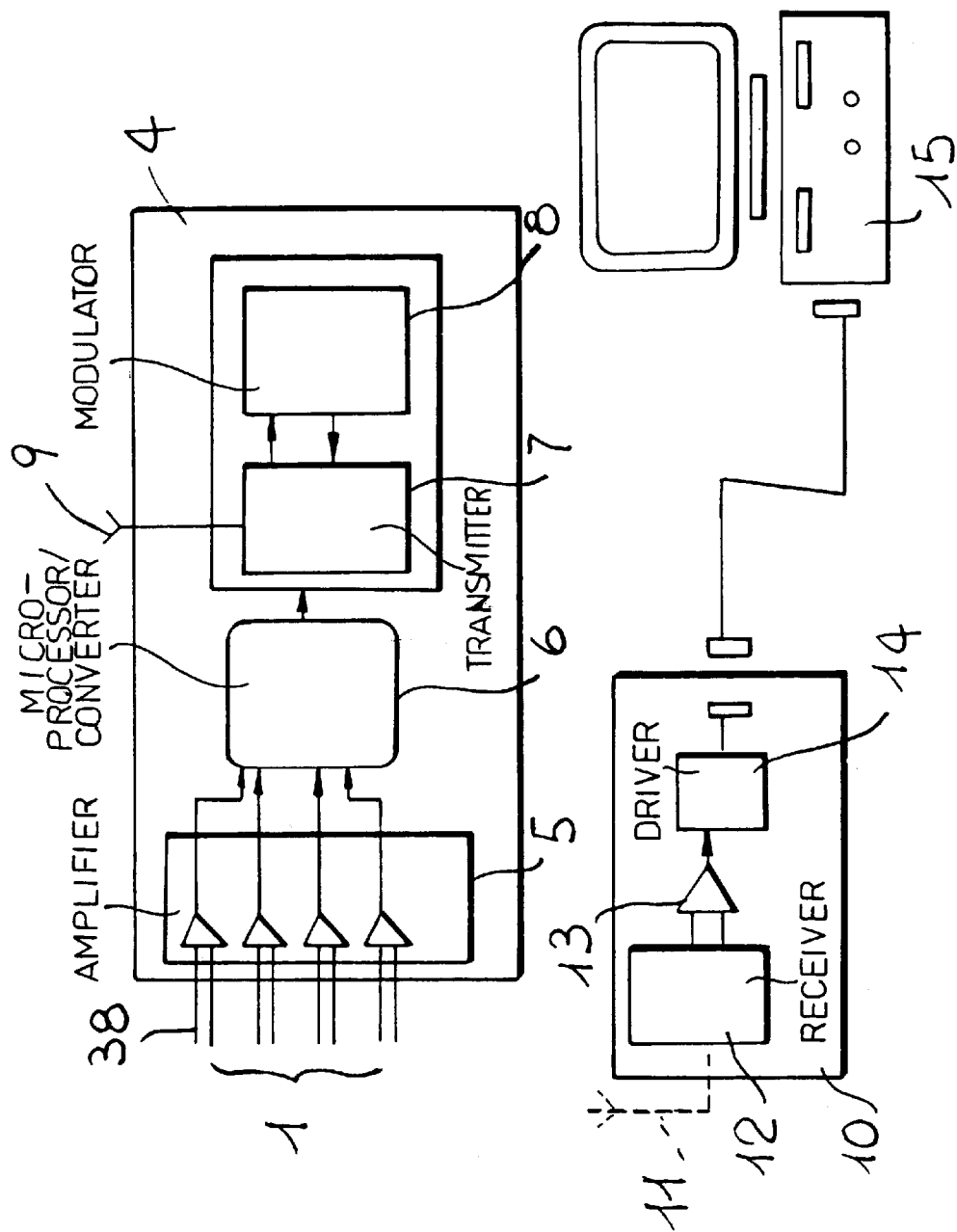
FIG. 1 is a schematic view of the set of main components of the device according to the invention, in the partially implanted version.

In the partially implanted version, the device according to the invention has the main components schematically illustrated in FIG. 1.

These include a certain number of electrocatheters or one single electrocatheter 1 equipped with one or more poles (four in number in the illustrated mode of embodiment) for recording the electrical activity of the viscera subject to electromyographic examination.

Figure 2:
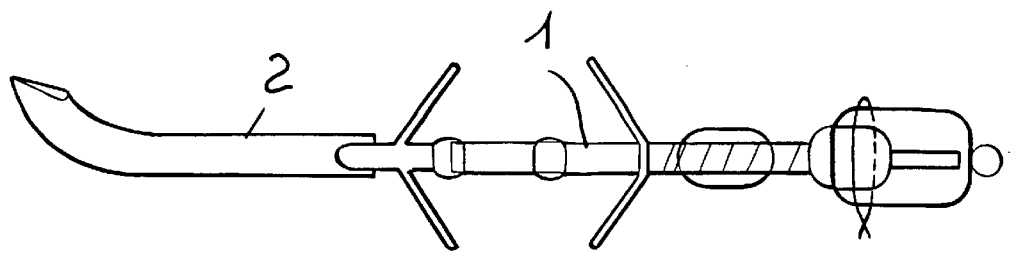
FIG. 2 is a diagrammatic elevational view which illustrates the electrocatheter used in the device of FIG. 1.

One of these electrocatheters, which is of the basically known type and is illustrated in FIG. 2, is equipped with corresponding needle 2 for inserting the catheter itself in the thickness of the muscle wall using the video-laparoscopic technique or laparotomy.

Figure 3:
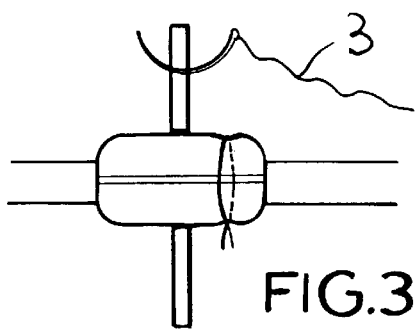
FIGS. 3 and 4 are diagrams which illustrate certain features of the electrocatheter of FIG. 2.
Figure 4:
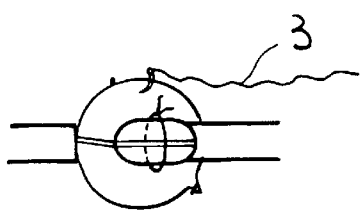

Needle 2 serves to facilitate insertion and anchoring of electrocatheter 1, and is designed to be removed once insertion is achieved. Electrocatheter 1 also has wire 3 (FIGS. 3 and 4) to anchor it to the abdominal wall.

Once implanted, electrocatheter 1 is connected by wires 38 to battery-powered amplifier-transmitter module 4. Module 4 includes amplifier 5 for one or more channels, microprocessor-converter 6, a unit comprising transmitter 7 and modulator 8, and transmitting antenna 9.

Amplifier 5 is made up of one or more modules with one or more inputs, and its function is to amplify the signals recorded by electrocatheters 1 implanted in the gastric viscera.

It also has an input impedance greater than or equal to 100 MOhms, as well as filters capable of eliminating the influence of the frequency of the household power source and other noise, with a gain greater than or equal to 200, and in any case compatible with the type of microprocessor to be used.

The signals processed by amplifier 5 are sent to microprocessor-converter 6, where the microprocessor is capable of converting the signals from analog to digital and of managing the flow or data to the transmitter 7—modulator 8 unit.

Microprocessor-converter 6 has a parallel-bus greater than or equal to 4 bits and includes an internal analog/digital converter, input/output ports depending from the number of channels to be processed, and a full duplex UART port with internal RAM greater than 128 bytes and external EPROM address capability.

As an alternative to amplifier 5 and the A/D conversion section of microprocessor-converter 6, it is also possible to use an A/D converter with a minimum reference voltage of 100 mV and resolution greater than or equal to 22 bits, or a microprocessor that does not require the presence of an A/D section.

The sampling frequency and characteristics of module 4 may be programmed either to monitor at a constant frequency or by packet, wherein the number of measurements in the packet is a function of the number of recording poles; the measurement period in the packet and the interval between packets may be programmed as usefully and opportunely as possible.

The clock frequency of the processor is greater than or equal to 2 MHz.

The function of transmitter 7—modulator 8, equipped with transmitting antenna 9, is to transform the digital signals into radio signals and to transmit them to receiver unit 10.

This transmitter-modulator must first of all have an operating frequency in MHz that is compatible with the frequencies allowed by the national legislation in force, and sufficient transmitting power to transmit within a predefined spatial range.

The signals transmitted by module 4 are received via antenna 11, by receiving module 10 consisting of receiver unit 12, clipping circuit 13, and serial interface driver 14.

Processing and graphic visualization unit 15, which receives, processes, and graphically visualizes the signals sent from module 10, also supplies power to the latter.

In the described mode of embodiment, as shown, module 4 supplies itself power, and once it is duly fixed to the skin of the patient (with a bandage or the like), it may be freely transported within the operating field of module 10.

For this reason, thanks to the radio link installed between module 4 and fixed unit 10, the patient is free to move about even during monitoring of the endogastric activity performed by the system.

Figure 5:
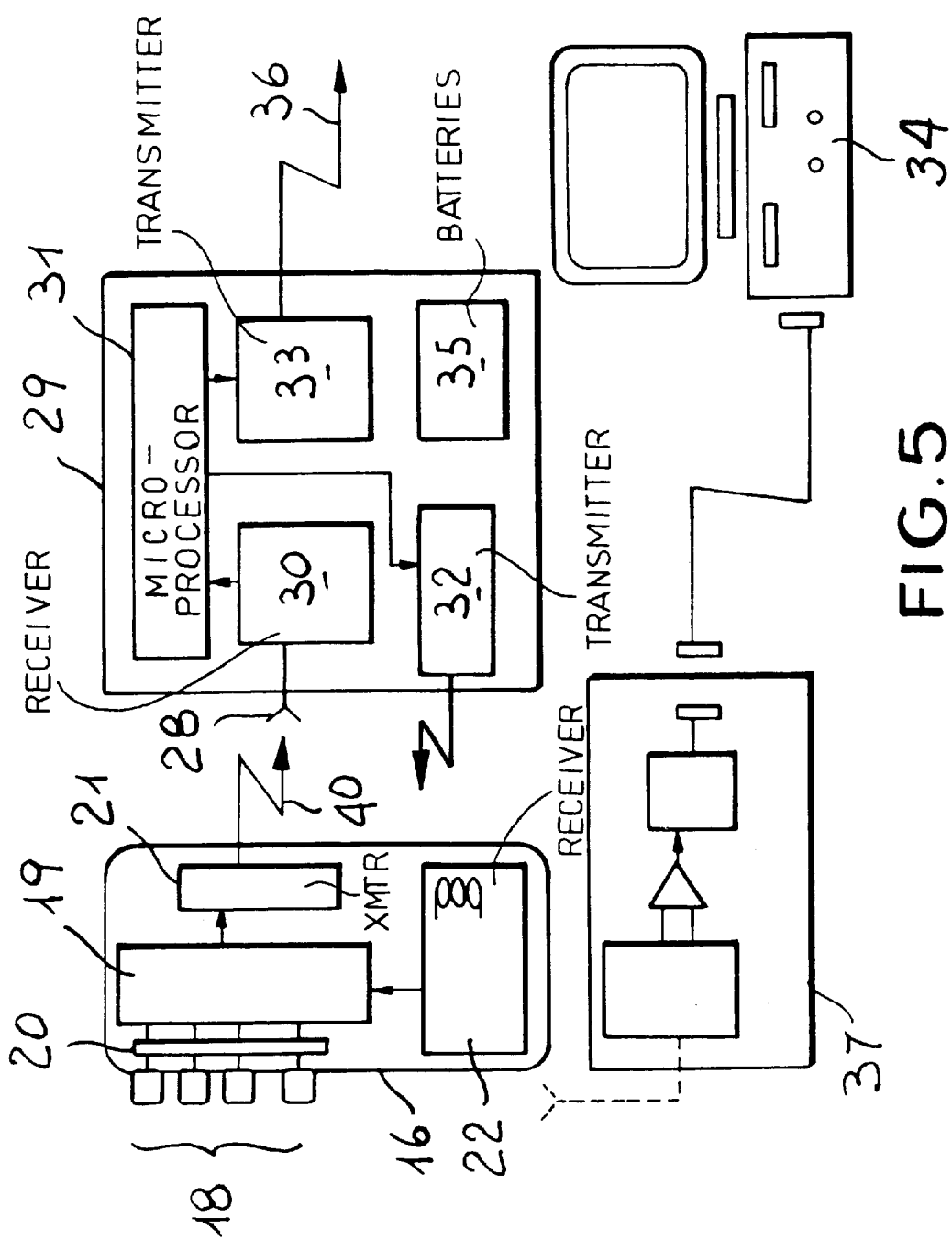
FIG. 5 is a schematic view of the set of main components of the device according to the invention, in the fully implanted version.

In the preferred embodiment illustrated in FIG. 5, the device according to the invention consists of miniaturized transducer 16 for mobile receiver 29 which together perform the same function as described for module 4 of the device in FIG. 1, with the following differences: the presence of the low-power Tx-Rx section (Tx on transducer or transmitter 16 and Rx on transducer or receiver 29), and the presence of a transponder to transmit from receiver 29 and to receive in transducer 16 the power needed by the transducer to perform the required operations.

More specifically, transducer 16 is composed of at least one electrode or sensor 18 (four in number in the illustrated example), which comes directly from the microcircuit.

The signals supplied by sensors 18 are processed by amplifier or by an AD converter 20 before being supplied to unit 19 (processor+AD converter, if not present on unit 20, multiplexer or all of them combined), and are then processed in low-power transmitter 21. Transducer 16 also consists of a transmitting antenna included on the chip and receiving section 22 of the transponder which receives and makes power available to supply the transducer itself when in operation.

By way of alternative to the transponder, and depending on the required operating autonomy, the use of a microbattery of the appropriate technology is also duly provided (Lithium).

This transducer is designed to be inserted into the thickness of the patient's gastric wall and, preferably, in a position corresponding to the small curve of the stomach.

Figure 6:
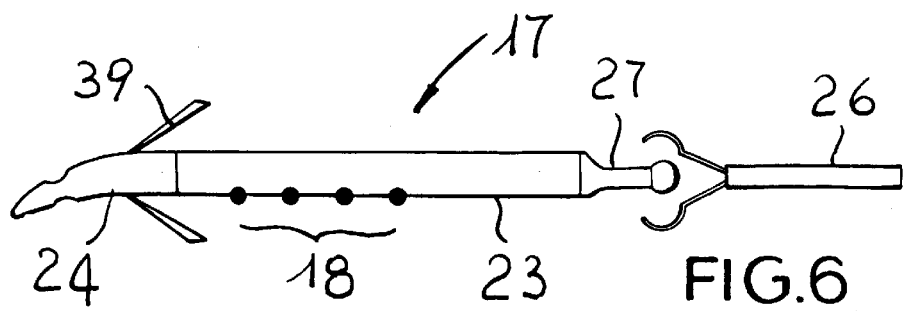
FIG. 6 is an elevation showing a device used in the unit of FIG. 5.

To that end, transducer 16 is enclosed within device 17 of FIG. 6, provided with casing 23 tapered to a mandrin and from which project, to the minimum required to ensure electrical contact with the muscle structure of the viscera, sensors 18 or the same transducer 16 of FIG. 5.

Casing 23 of device 17 is made of an electrical insulating material that is biologically compatible and has the necessary mechanical rigidity and flexibility for this purpose.

The length and diameter of mandrin 17 shall be appropriate for installation by a gastroscope having the characteristics described below.

Figure 7:
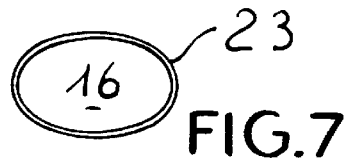
FIG. 7 is a cross section of the needle in the device in FIG. 6.

The mandrin may, for example, be about 5 cm in length with a maximum diameter of about 2.5 mm, and with a shape roughly similar to that of needle 2 in FIG. 2, from which it differs primarily by the fact that point 24 may also be of a plastic material and that its cross section is oval in shape (FIG. 7).

Figure 8:
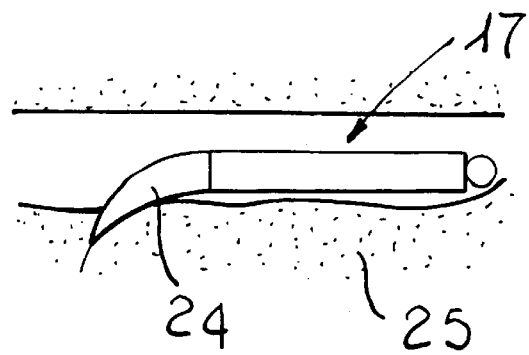
FIG. 8 is a diagram which shows the device of FIG. 6 as it is positioned during recording of the endogastric activity.

In this case, the needle-shaped transducer is introduced in the gastric cavity 25 (FIG. 8) and inserted below the mucous membrane into the muscular thickness of the gastric wall. Ultimately, the final location is always the same, which is to say in the muscular layer of the wall of the stomach.

Transducer 16 remains in such a location for a sufficient number of days to permit the trauma tunnel to heal and to obtain valid recordings of the electrical activity of the stomach.

In order to introduce monitoring device 17 in the gastric cavity, standard gastroscope 26 may be used, provided for example that it has an operating channel of 2.8 mm or greater and/or is specially designed, and has a probe very similar to the type used for mucous membrane biopsy.

Transducer 17 may also be held by one end 27 and driven in below the gastric mucosa while the transducer remains in the gastric wall and inside the viscera.

A small portion of the transducer will remain outside the submucosa (muscular) tunnel, and two small wings 39 will prevent its total disappearance into the wall.

After a certain number of days, once the electromyographic monitoring is completed, the transducer may be removed from its seat using endoscopic biopsy pincers.

Radio signal 40 sent by transducer 16 is received by antenna 28 of mobile receiving module 29 of FIG. 5.

This module is applied externally to the patient's skin, in an epicritical position (as close as possible to implanted transducer 16), and supported by the appropriate means (brace, belt, or the like).

In addition to receiving antenna 28 inserted in the module itself, module 29 also includes receiver unit 30, transmitting section 32 of the transponder, and transmitter 33 of radio signal 36 to fixed processing unit 34.

For their part, these components are controlled and managed, also by means of local firmware, by microprocessor 31.

Rechargeable batteries 35 are also provided to power module 29.

The transmission by radio wave 36 is received by fixed receiver 37, similar to receiver 10 of FIG. 1, and from there it is sent to above-described unit 34 for processing and graphic visualization of the signal.

Transmission is provided:
  by radio wave, combined with a processing unit positioned locally within an area of about ten meters;
  by devices that use the EHS (European Home System) protocol for communication between devices inside buildings using the cabled and wireless equipment provided;—remotely, using techniques currently in existence in GSM or similar type telephones, or the like, using a high-power transmitter with special components.

The inductive or analog type transponders (photovoltaic types cannot be used for obvious technical reasons, nor can ultrasound since it is contra-indicated) transmit to the transducer the power needed to make the required readings and to transmit them; power is delivered prior to the reading phase, and during that phase if necessary.

It should also be noted that along with monitoring electrical activity, it simultaneously also possible to obtain a record of the peristaltic activity of the viscera by recording changes in tension caused by the impedance oscillation in the vicinity of the electrode resulting from changes in muscle tissue density caused by peristaltic contraction.

What is claimed is:

1. An implantable device for internal-external electromyographic recording of electromotor activity of the digestive system of a patient, comprising:

a casing adapted to be received in and fully implanted in viscera of said digestive system;

at least one sensor projecting from said casing by a minimum amount necessary to permit said sensor to electrically contact muscle structure of said viscera and generate electromyographic signals;

at least one radio signal conversion and transmission unit in said casing connected to said sensor and converting into radio signals electromyographic signals received from said sensor and transmitting said radio signals from said digestive system; and a processor at a location spaced from the patient, receiving said radio signals transmitted from said digestive system, and registering electromotor activity in said muscle structure represented by said radio signals wherein said casing is provided with a clip-off tip, with an end enabling grasping of the casing by a gripping device and with wings for holding said casing in a wall of said viscera.

2. The implantable device defined in claim 1 wherein said unit comprises at least one self powered amplifier-transmitter module received in said casing and connected to said sensor.

3. The implantable device defined in claim 2 wherein said module comprises an amplifier for amplifying a signal from said sensor and outputting an amplified analog signal, a processor-converter for converting said analog signal as supplied by said amplifier to digital signals, a transmitter-modulator unit connected to said processor-converter to convert said digital signals into said radio signals, and an antenna receiving said radio signals from said transmitter-modulator and transmitting said radio signals to said processor.

4. The device defined in claim 3 wherein said amplifier has an input impedance of at least 100 M ohms and a gain of at least 200.

5. The device defined in claim 3 wherein said processor converter has a parity of at least four bits, an internal analog/digital converter, input/output ports as a function of a number of channels to be processed and a full duplex UART port with internal RAM greater than 128 bytes and an external EPROM entries.

6. The device defined in claim 3 wherein said processor converter has a clock frequency of at least two MHz.

7. The device defined in claim 3 wherein said processor at said location spaced from patient has a receiver unit provided with an antenna, a comparator connected to said receiver unit, a serial interface driver and an antenna for transmission of radio signals to a unit for processing and graphically displaying the electromotor activity in said muscle structure.

8. The device defined in claim 1 wherein said casing has dimensions enabling it to be passed through a channel in a gastroscope and is composed of an electrically insulating and biologically compatible material.

9. The device defined in claim 1 wherein said processor includes a self powered portable unit adapted to be affixed on an exterior of the skin of the patient to receive said radio signals and for transmitting said radio signals to a fixed receiver.

10. The device defined in claim 1 wherein said portable unit comprises an antenna receiving the radio signal from said casing, a receiver connected to said antenna, a transmitter forming a transponder for powering the unit in said casing, a microprocessor controlling said portable unit and batteries supplying electrical power to said portable unit.

11. The device defined in claim 1, further comprising said fixed receiver, and wherein said fixed receiver has a unit receiving signals from said portable unit, a clipping circuit connected to said unit, a serial interface driver connected to said clipping circuit and means for transmitting signals for processing and graphically displaying the electromotor activity.

* * * * *